US010471172B2

(12) United States Patent
Kashiwabuchi et al.

(10) Patent No.: US 10,471,172 B2
(45) Date of Patent: Nov. 12, 2019

(54) METHODS OF MAKING DRUG LOADED MICROFIBER SUTURES FOR OPHTHALMIC APPLICATION

(71) Applicant: The Johns Hopkins University, Baltimore, MD (US)

(72) Inventors: Fabiana Kimie Kashiwabuchi, Baltimore, MD (US); Justin Hanes, Baltimore, MD (US); Hai-Quan Mao, Baltimore, MD (US); Peter John McDonnell, Baltimore, MD (US); Qingguo Xu, Baltimore, MD (US); Shuming Zhang, Baltimore, MD (US); Kunal S. Parikh, Reynoldsburg, OH (US)

(73) Assignee: The Johns Hopkins University, Baltimore, MD (US)

( * ) Notice: Subject to any disclaimer, the term of this patent is extended or adjusted under 35 U.S.C. 154(b) by 343 days.

(21) Appl. No.: 15/375,472

(22) Filed: Dec. 12, 2016

(65) Prior Publication Data

US 2017/0087271 A1 Mar. 30, 2017

Related U.S. Application Data

(63) Continuation of application No. 13/888,164, filed on May 6, 2013, now Pat. No. 9,533,068.

(60) Provisional application No. 61/642,535, filed on May 4, 2012.

(51) Int. Cl.
*D01D 5/04* (2006.01)
*D01D 5/06* (2006.01)
*D01D 10/06* (2006.01)
*A61L 17/00* (2006.01)
*B29C 48/00* (2019.01)
*B29C 48/14* (2019.01)
*D01D 5/00* (2006.01)
*D02G 3/44* (2006.01)
*A61K 31/5383* (2006.01)
*B29K 67/00* (2006.01)
*B29K 105/00* (2006.01)
*B29L 31/00* (2006.01)

(52) U.S. Cl.
CPC ........ *A61L 17/005* (2013.01); *A61K 31/5383* (2013.01); *B29C 48/022* (2019.02); *B29C 48/142* (2019.02); *B29C 48/147* (2019.02); *D01D 5/0007* (2013.01); *D01D 5/0038* (2013.01); *D01D 5/0046* (2013.01); *D01D 5/0076* (2013.01); *D02G 3/448* (2013.01); *A61L 2300/604* (2013.01); *A61L 2430/16* (2013.01); *B29K 2067/046* (2013.01); *B29K 2105/0035* (2013.01); *B29K 2995/006* (2013.01); *B29K 2995/0056* (2013.01); *B29L 2031/7546* (2013.01)

(58) Field of Classification Search
CPC .... D01D 5/003; D01D 5/0038; D01D 5/0046; D01D 5/0076; D01D 5/04; D01D 5/06; D01D 10/06; D02G 3/448
USPC ..... 264/10, 211.12, 234, 464, 465, 466, 484
See application file for complete search history.

(56) References Cited

U.S. PATENT DOCUMENTS

| | | | |
|---|---|---|---|
| 4,027,676 A | 6/1977 | Mattei | 606/230 |
| 4,201,216 A | 5/1980 | Mattei | 606/230 |
| 4,857,602 A | 8/1989 | Casey et al. | 525/408 |
| 4,994,074 A | 2/1991 | Bezwada et al. | 606/230 |
| 4,997,652 A | 3/1991 | Wong | |
| 5,034,506 A | 7/1991 | Summerton | |
| 5,412,072 A | 5/1995 | Sakurai | |
| 5,522,842 A | 6/1996 | Shalaby | 606/230 |
| 5,552,160 A | 9/1996 | Liversidge | |
| 5,578,325 A | 11/1996 | Domb | |
| 5,710,135 A | 1/1998 | Leenders | |
| 5,932,462 A | 8/1999 | Harris et al. | 435/188 |
| 6,007,845 A | 12/1999 | Domb | |
| 6,235,869 B1 | 5/2001 | Roby et al. | 528/354 |
| 7,550,154 B2 | 6/2009 | Saltzman | |
| 7,638,137 B2 | 12/2009 | Chauhan | |

(Continued)

FOREIGN PATENT DOCUMENTS

WO 9207866 5/1992
WO 98059064 12/1998

(Continued)

OTHER PUBLICATIONS

Yang et al, "Biodegradable Nanoparticles Composed Entirely of Safe Materials That Rapidly Penetrate Human Mucus", Angew Chem. Int. Ed. Engl. (Mar. 7, 2011), pp. 2597-2600.*

Iwase et al, "Safe and Effective Polymeric-Doxorubicin Conjugate Nanoparticies for Prolonged Antiangiogenic Activity in Eye" (abstract), presentation at the Assocoation for Research in Vision and Opthalmology annual meeting (2012).*

(Continued)

Primary Examiner — Leo B Tentoni
(74) Attorney, Agent, or Firm — Pabst Patent Group LLP

(57) ABSTRACT

Ophthalmic suture materials made from biocompatible and biodegradable polymers with high tensile strength for use in drug delivery, methods of making them, and method of using them for ocular surgery and repair have been developed. The suture materials are made from a combination of a biodegradable, biocompatible polymer and a hydrophilic biocompatible polymer. In a preferred embodiment the suture materials are made from a poly(hydroxyl acid) such as poly(1-lactic acid) and a polyalkylene oxide such as poly(ethylene glycol) or a polyalkylene oxide block copolymer. The sutures entrap (e.g., encapsulate) one or more therapeutic, prophylactic or diagnostic agents and provide prolonged release over a period of at least a week, preferably a month.

16 Claims, 3 Drawing Sheets

(56) References Cited

U.S. PATENT DOCUMENTS

| | | | |
|---|---|---|---|
| 7,645,736 B2 | 1/2010 | Bender | |
| 7,648,959 B2 | 1/2010 | Bender | |
| 8,071,795 B2 | 12/2011 | VanMeir | |
| 8,394,799 B2 | 3/2013 | Lee | |
| 2003/0042137 A1 | 3/2003 | Mao et al. | 204/403.01 |
| 2003/0118550 A1 | 6/2003 | Kabanov | |
| 2004/0162580 A1 | 8/2004 | Hain | 606/229 |
| 2004/0209806 A1 | 10/2004 | Rothenberg | |
| 2004/0209807 A1 | 10/2004 | Quay | |
| 2004/0258763 A1 | 12/2004 | Bell | |
| 2005/0070448 A1 | 3/2005 | Kupper et al. | 508/463 |
| 2005/0149118 A1 | 7/2005 | Koyfman et al. | 606/228 |
| 2005/0149119 A1 | 7/2005 | Koyfman et al. | 606/228 |
| 2005/0253305 A1* | 11/2005 | Kim | D01D 5/0046 264/465 |
| 2007/0087989 A1 | 4/2007 | Huang | |
| 2007/0111959 A1 | 5/2007 | Yockman | |
| 2007/0238654 A1 | 10/2007 | Deschatelets | |
| 2008/0166414 A1 | 7/2008 | Hanes | |
| 2008/0268243 A1 | 10/2008 | Stopek et al. | 428/378 |
| 2008/0287341 A1 | 11/2008 | Chen | |
| 2008/0287990 A1 | 11/2008 | Smit | 606/228 |
| 2009/0011040 A1 | 1/2009 | Naash | |
| 2009/0060979 A1 | 3/2009 | Bezwada | 424/426 |
| 2009/0087494 A1 | 4/2009 | Kompella | |
| 2009/0138041 A1 | 5/2009 | Stopek et al. | 606/231 |
| 2009/0220572 A1 | 9/2009 | Deschatelets | |
| 2009/0226531 A1 | 9/2009 | Lyons | |
| 2009/0234375 A1 | 9/2009 | Simon | 606/151 |
| 2009/0246259 A1* | 10/2009 | Kita | D01D 5/003 264/465 X |
| 2009/0291919 A1 | 11/2009 | Kaushal | |
| 2010/0034749 A1 | 2/2010 | Schulze | |
| 2010/0094340 A1 | 4/2010 | Stopek et al. | 606/231 |
| 2010/0152831 A1 | 6/2010 | Guo et al. | 623/1.13 |
| 2010/0166854 A1* | 7/2010 | Michniak-Kohn | D01D 5/0061 264/465 X |
| 2010/0209469 A1 | 8/2010 | Bezwada | 424/423 |
| 2010/0215580 A1 | 8/2010 | Hanes | |
| 2011/0264139 A1 | 10/2011 | Hunter et al. | 606/228 |
| 2012/0041481 A1 | 2/2012 | Daniloff et al. | 606/214 |
| 2012/0121661 A1 | 5/2012 | Schwartz et al. | 424/400 |
| 2012/0201873 A1 | 8/2012 | Hohlbaum et al. | 424/450 |
| 2012/0245629 A1 | 9/2012 | Gross et al. | 606/228 |
| 2012/0288464 A1 | 11/2012 | Carmichael et al. | 424/70.16 |
| 2012/0303010 A1 | 11/2012 | Vijfvinkel | 606/6 |
| 2013/0041407 A1 | 2/2013 | Montenegro et al. | 606/231 |
| 2013/0084636 A1* | 4/2013 | Cho | A61F 2/30756 435/372 |
| 2013/0178949 A1* | 7/2013 | Bowlin | D01D 5/0076 623/23.72 |
| 2013/0226234 A1 | 8/2013 | Avelar et al. | 606/231 |
| 2014/0212661 A1 | 7/2014 | Khan | 428/341 |

FOREIGN PATENT DOCUMENTS

| | | | |
|---|---|---|---|
| WO | 9901498 | 1/1999 | |
| WO | 0046147 | 8/2000 | |
| WO | 0202432 | 3/2002 | |
| WO | 2002038127 | 5/2002 | |
| WO | 02060412 | 8/2002 | |
| WO | 2005012407 | 2/2005 | |
| WO | 2005072710 | 8/2005 | |
| WO | 2006109177 | 10/2006 | |
| WO | 2006122542 | 11/2006 | |
| WO | 2007016380 | 2/2007 | |
| WO | 2007133812 | 11/2007 | |
| WO | 2008030557 | 3/2008 | |
| WO | 2009151539 | 12/2009 | |
| WO | 2010086406 | 8/2010 | |
| WO | WO-2011105724 A2 * | 9/2011 | A61L 27/56 |

OTHER PUBLICATIONS

Erdmann and Uhrich, "Synthesis and degradation characteristics of salicylic acid-derived poly(anhydride-esters)", Biomaterials, 21:1941-6 (2000).

Grisanti and Ziemssen, "Bevacizumab: Off-label uses in ophthalmology", Indian J Ophtalmol., 55(6):417-20 (2007).

Jan and Kumar, "Self assembly of amphiphilic (PEG)(3)-PLA copolymer as polymersomes: Preparation, characterization, and their evaluation as drug carrier", Biomacromaolecules, 11:1027-35 (2010).

Sagong, et al., "Intravltreal becacizumab for the treatment of neovascular glaucoma associated with central retinal artery occlusion", Korean J Ophthalmol., 23:215-8 (2009).

Aich, et al., "Developmnt of delivery methods for carbohyfrate-based drugs; controlled release of biologically-active shott chain fatty acid-hexosamine analogs", Glycoconj. J., 27(4):445-59 (2010).

Apgar, et al., "Multiple-particle tracking measurements of heterogeneities in solutions of actin filaments and actin bundles", Biophys. J., 79:1095-1106 (2000).

Ben-Shabat, S. et al.,PEG-PLA block copolymer as potential drug carrier: preparation and characterization. Macromol. Biosci. 6:1019-1025 (2006).

Beyerle, et al., "PEGylation affects cytotoxicity and cell-compatibility of poly(ethylene imine) for lung application: structure-function relationships", Toxicol. Appl. Pharmacol. 242:146-54 (2010).

Blessing, et al., "Monomolecular collapse of plasmid DNA into stable virus-like particles", PNAS, 95:1427-31 (1998).

Bourges, et al., "Pcular drug delivery targeting the retina and retina pigment epithelium using polyactide nanoparticles", Inv. Ophthalmology Vis Sci., 44(8):3562-9 (2003).

Cone, "Barrier properties of mucus", Adv. Drug Deliv. Rev., 61:75-78 (2009).

Dauty, et al., "Dimerizable cationic detergents with a low cmc condense plasmid DNA into nanometric particles and transfect cells in culture", J. Am. Chem. Soc. 123:9227-34 (2001).

de Kozak, et al., "Intraocular injection of tamoxifen-loaded nanoparticles: a new treatment of experimental autoimmune uveoeretinitis", Eur. J Immunol., 34:3702-12 (2004).

Deosarkar, et al., "Polymeric particles conjugated with a ligand to VCAM-1 exhibit selective, avid, and focal adhesion to sites of atherosclerosis", Biotech. Bioeng., 101(2):400-7 (2008).

Desai, "Pluronic F127-based ocular delivery system containing biodegradable polyisobutylcyanoacrylate nanocapsules of pilocarpine", Drug Delivery, 7:201-7 (2000).

Dong, et al., "Vascular cell-adhesion molecule-1 plays a central role in he proangiogenic effects of oxidative stress", PNAS, 108(35):14614-9 (2011).

Escobar-Chavez, "Application of thermo-reversible pluronic F-127 gels in pharmaceutical formulations", J Pharma Sci., 9(3):339-58 (2006).

Ferrari, et al., "Barriers to and new approaches for gene therapy and gene delivery in cystic fibrosis", Adv. Drug Deliv. Rev. 54:1373-93 (2002).

Ferrari, et al., "Immunological hurdles to lung gene therapy", Clin. Exp. Immunol., 132:1-8 (2003).

Ferrari, et al., "Polyethyienimine shows properties of interest for cystic fibrosis gene therapy", Biochemica Biophysica Acta., 1447(2-3):219-25 (1999).

Fiegel, et al., "Poly(ether-anhydride) dry powder aerosols for sustained drug delivery in the lungs", J Control Release, 96:411-23 (2004).

Fischer, et al., "A novel non-viral vector for DNA delivery based on low molecular weight, branched polyethylenimine: effect of molecular weight on transfection efficiency and cytotoxicity", Pharm. Res. 16:1273-9 (1999).

Flotte, et al., "Gene therapy in cystic fibrosis", Chest, 120(3 suppl) 124S-131S (2001).

Giannavola, et al., "Influence of preparation conditions on Acyclovir-loaded poly-d, l-lactic acid nanospheres and effect of PEG coating on ocular drug bioavailability", Pharma. Res., 20(4):584-90 (2003).

Gou, et al., "Synthesis, self-assembly, and drug-loading capacity of well-defined cyclodextrin-centered drug-conjugated amphiphilic A 19 B 7 miktoarm star copolymers based on poly([epsilon]-

(56) References Cited

OTHER PUBLICATIONS caprolactone) and Poly(ethylene glycol)", Biomacromolecules 11(4):934-43 (2010).
Govender, et al., "PLGA nanoparticles prepared by nanoprecipitation: drug loading and relase studies of a water soluble drug", J Cont. Rel., 57:171-85 (1999).
Gregory, et al., "Expression and characterization of the cystic fibrosis transmembrane conductance regulator", Nature, 347:362-6 (1990).
Griesenbach and Alton, "Gene transfer to the lung: lessons learned from more than 2 decades of CF gene therapy", Adv. Drug Deliv. Rev. 61:128-39 (2009).
Hida, et al., "Common gene therapy viral vectors do not efficiently penetrate sputum from cystic fibrosis patients", PLoS ONE. 6:e19919 (2011).
Jiang, et al., "Efficiency of cationic lipid-mediated transfection of polarized and differentiated airway epithelial cells in vitro and in vivo", Hum. Gene. Ther. 9:1531-42 (1998).
Kichler, et al., "Intranasal gene delivery with a polyethylenimine-PEG conjugate", J. Control. Release, 81:379-8 (2002).
Kleemann, et al., "Modified polyethylenimines as non-viral gene delivery systems for serosol gene therapy: Investigations of the complex structure and stability during air-jet and ultrasonic nabulization", J Controlled Release, 100(3):437-50 (2004).
Kleemann, et al., "Nano-carriers for DNA delivery to the lung based upon a TAT-derived peptide covalently coupled to PEG-PEI", J Controlled Release, 109(1-3):299-316 (2005).
Kompella, et al., "Luteinizing hormone-releasing hormone agonist and transferrin functionalizations enhance nanoparticle delivery in a novel bovine ex vivo eye model", Mol. Vis., 12:1185-98 (2006).
Lai, et al., "Mucus-penetrating nanoparticles for drug and gene delivery to mucosal tissues", Adv. Drug Deliv. Rev. 61:158-71 (2009).
Lai, et al., "Nanoparticles reveal that human cervicovaginal mucus is riddled with pores larger than viruses", PNAS, 107:598-603 (2010).
Lai, et al., "Rapid transport of large polymeric nanoparticles in fresh undiluted human mucus", PNAS, 104(5):1482-7 (2007).
Matsui, et al., "Loss of binding and entry of liposome-DNA complexes decreases transfection efficiency in differentiated airway epithelial cells", J. Biol. Chem. 272:1117-26 (1997).
Newman, et al., "Uptake of poly(D,L-lactic-co-glycolic acid) microspheres by antigen-presenting cells in vivo", J Biomed Mater Res., 60(3):480-6 (2002).
Ogris, et al., "PEGylated DNA/transferrin-PEI complexes: reduced interaction with blood components, extended circulation in blood and potential for systemic gene delivery", Gene Ther., 6:595-605 (1999).
Okamoto, et al., Transgenic mice with increased expression of vascular endothelial growth factor in the retina: a new model of intraretinal and subretinal neovasularization, Am. J. Pathol. 151:281-291 (1997).
Rich, et al., "Expression of cystic fibrosis transmembrane conductance regulator corrects defective chloride channel regulation in cystic fibrosis airway epithelial cells", Nature, 347:358-62 (1990).
Riordan, et al., "Identification of the cystic fibrosis gene: cloning and characterization of complementary DNA", Science 245:1066-73 (1989).
Saishin, et al., "VEGF-TRAP(R1R2) suppresses choroidal neovascularization and VEGF-induced breakdown of the blood-retinal barrier", J. Cell Physiol., 195:241-8 (2003).
Sanders, et al., "Cystic fibrosis sputum: a barrier to the transport of nanospheres", Am. J. Respir. Crit. Care Med., 162:1905-11 (2000).
Sanders, et al., "Extracellular barriers in respiratory gene therapy", Adv. Drug Deliv. Rev. 61:115-27 (2009).
Scheule, et al., "Basis of pulmonary toxicity associated with cationic lipid-mediated gene transfer to the mammalian lung", Hum. Gene Ther., 8:689-707 (1997).
Singh, et al., "Cationic microparticles: A potent delivery system for DNA vaccines", PNAS, 98(2):811-6 (2000).
Smith, et al., Oxygen-induced retinopathy in the mouse, Invest. Ophthalmol. Vis. Sci. 35:101-111 (1994).
Sobczak, et al., "Synthesis and characterization of polyester conjugates of ciprofloxacin", Eu. J. Med Chem., 45(9):3844-9 (2010).
Soppimath, et al., "Biodegradable polymeric nanoparticles as drug delivery devise", J Cont. Release, 70:1-20 (2001).
Sterchak, et al., "Unchanged stereoregular nucleic acid analogues I Synthesis of a cytosine-containing oligomer with carbonate internucleoside linkages", J Organic Chem., 52:4202, (1987).
Suh, et al., "Efficient active transport of gene nanocarriers to the cell nucleus", PNAS, 100:3878-82 (2003).
Suh, et al., "PEGylation nanoparticles improves their cytoplasmic transport", Int. J Nanomed., 2(4):735-41 (2007).
Suh, et al., "Real-time multiple-particle tracking: applications to drug and gene delivery", Adv. Drug Deliv. Rev. 57(1):63-78 (2005).
Suk, et al., "N-acetylcysteine enhances cystic fibrosis sputum penetration and airway gene transfer by highly compacted DNA nanoparticles", Mol. Ther. 19:1981-9 (2011a).
Suk, et al., "Overcoming the cystic fibrosis sputum barrier to nanoparticle-based gene carriers", (Ph. D. thesis) John Hospkins, Baltimore, Maryland (02-10-2011b).
Suk, et al., "Quantifying the intracellular transport of viral and nonviral gene vectors in primary neurons", Exp. Biol. Med., 232:461-9 (2007).
Suk, et al., "The penetration of fresh undiluted sputum expectorated by cystic fibrosis patients by non-adhesive polymer nanoparticles", Biomaterials. 30:2591-7 (2009).
Tanaka, et al., "Development of cell-penetrating peptide-modified MPEG-PCL diblock copolymeric nanoparticles for systemic delivery", Intl J Pharmac., 396(1-2):229-38 (2010).
Tang, et al., "Biodegradable polymer nanoparticles that rapidly penetrate the human mucus barrier", PNAS, 106:19268-73 (2009).
Tang, et al., "Enhanced efficacy of local etoposide delivery by poly(ether-anhydride)particles against small cell lung cancer in vivo", Biomaterials, 31:339-44 (2010).
Tang, et al., "Polyethylene glycol modified polyethylenimine for improved CNS gene transfer: effects of PEGylation extent", Biomaterials, 24(13):2351-62 (2003).
Terry, "Ternary particles for effective vaccine delivery to the pulmonary system", (Ph.D. Thesis, UMI ProQuest, Ann Arbor (2008).
Tobe, et al., "Targeted disruption of the FGF2 gene does not prevent choroidal neovascularization in a murine model", Am. J. Pathol. 153:1641-1646 (1998).
Veronese, et al., "PEG-doxorubicin conjugates: influence of polymer structure on drug release in vitro cytotoxicity, biodistribution, and antitumor activity", Bioconjig Chem., 16(4):775-84 (2005).
Voynow and Rubin, "Mucins, mucus, and sputum", Chest. 135:505-12 (2009).
Yokoyama, et al., "Characterization and anticancer activity of the micelle-forming polymeric anticancer drug adriamycln-conjugated poly(ethylene glycol)-poly(aspartic acid) block copolymer", Cancer Res., 50:1693-1700 (1990).
Yoshida, et al., Digoxin inhibits retinal ischemia-induced HIF-1alpha expression and ocular neovascularization, FASEB J. 24:1759-1767 (2010.

* cited by examiner

METHODS OF MAKING DRUG LOADED MICROFIBER SUTURES FOR OPHTHALMIC APPLICATION

CROSS-REFERENCE TO RELATED APPLICATIONS

This application is a continuation of application Ser. No. 13/888,164, filed May 6, 2013, now U. S. Pat. No. 9,533,068, which claims priority to and the benefit of U. S. Provisional Application No. 61/642,535, filed May 4, 2012, which are incorporated herein by reference in their entirety.

FIELD OF THE INVENTION

The present invention relates to surgical sutures for controlled drug delivery, and in particular to ophthalmic sutures providing controlled delivery.

BACKGROUND OF THE INVENTION

Invasive ophthalmic surgeries often lead to numerous complications for patients, at least in part because patient compliance with prophylactic drugs after ophthalmic surgery is relatively low and in part because the ocular bioavailability is frequently low for common dosage forms. The vast majority of ophthalmic drug formulations remain the traditional solutions, ointments and suspensions, by one estimate accounting for about 90% of the global market of ophthalmic drug formulations.

Even when patient compliance is high, the ocular bioavailability of drugs applied topically as eye-drops is very poor. The absorption of drugs in the eye is severely limited by some protective mechanisms that ensure the proper functioning of the eye. The contact with the absorbing surfaces (cornea and sclera) is reduced to a maximum of about two minutes. Dosage volumes are limited by drainage via the nasolacrimal system into the nasopharynx and the gastrointestinal tract. Lacrimation and the physiological tear turnover (16% per minute in humans in normal conditions) are often increased by the instillation even of mildly irritating solutions, leading to more rapid clearance of the applied dosage form.

Trabeculectomy is an ophthalmic surgical procedure used in the treatment of glaucoma. Removing part of the eye's trabecular meshwork and adjacent structures allows drainage of aqueous humor from within the eye to underneath the conjunctiva to relieve intraocular pressure. The scleral flap is typically sutured loosely back in place with several sutures. Common complications include blebitis (an isolated bleb infection typically caused by microorganisms such as *Staphylococcus epidermidis, Propriobacterium acnes*, or *Staphylococcus aureus*), inflammation, and bleb-associated endophthalmitis.

Endophthalmitis is an inflammation of the ocular cavities and their adjacent structures. It is a possible complication of all intraocular surgeries, particularly cataract surgery, which can result in loss of vision or the eye itself. Endophthalmitis is usually accompanied by severe pain, loss of vision, and redness of the conjunctiva and the underlying episclera. Infectious etiology is the most common and various bacteria and fungi have been isolated as the cause of the endophthalmitis. The patient needs urgent examination by an ophthalmologist and/or vitreo-retina specialist who will usually decide for urgent intervention to provide intravitreal injection of potent antibiotics and also prepare for an urgent pars plana vitrectomy as needed. Enucleation may be required to remove a blind and painful eye.

Opthalmic sutures are commonly used during ophthalmic surgical procedures, including trabeculectomy as well as pterygium removal, cataract surgery, strabismus correction surgery, penetrating keratoplasty, sclerectomy, and conjunctival closure. The choice of suture material can strongly impact the occurrence of complications related to infection and inflammation post ophthalmic surgery, either causing irritation and local inflammation or providing a substrate for microorganism growth. The suture materials typically employed include nonbiodegradable ophthalmic suture materials such as ETHILON® nylon suture, MERSILENE® polyester fiber suture, PERMA-HAND® silk suture, PROLENE® polypropylene suture, each commercially available from Ethicon, Somerville, N.J.; and VASCUFIL® coated monofilament suture composed of a copolymer of butylene terephthalate and polyteramethylene ether glycol, MONOSOF~DERMALON® monofilament nylon sutures composed of long-chain aliphatic polymers Nylon 6 and Nylon 6.6, NOVAFIL® monofilament sutures composed of a copolymer of butylene terephthalate and polyteramethylene ether glycol, SOF SILK® braided sutures composed of fibroin, TI-CRON-SURGIDAC® braided polyester sutures composed of polyester terephthalate, SURGILON® braided nylon sutures composed of the long-chain aliphatic polymers Nylon 6 and Nylon 6.6 and SURGIPRO II-SURGIPRO® sutures composed of polypropylene, each commercially available from U.S. Surgical, Norwalk, Conn.

Ideally, ophthalmic suture materials would be biodegradable and biodegradable over the useful suture lifetime, retaining the requisite tensile strength and capable of delivering therapeutic or prophylactic agents to increase patient success. For pterygium removal, cataract surgery and strabismus correction surgery, sutures could be used to close the wound and release antibiotic and anti-inflammatory drugs. For trabeculectomy surgeries, sutures could be placed on sclera flaps providing local chemotherapeutic agents, decreasing production of scar tissue, and also, on conjunctival closure with antibiotic release. In penetrating keratoplasty, the sutures hold the graft, as well as release antibiotic and immunosuppressant agents.

Therefore, it is an object of the invention to provide ophthalmic sutures that are biocompatible and biodegradable and retain the requisite tensile strength over the useful life of the suture.

It is further an object of the invention to provide ophthalmic sutures capable of delivering an effective amount of one or more therapeutic or prophylactic agents to the ocular region over an extended period of time.

It is further an object of the invention to provide ophthalmic sutures having a diameter allowing for use in ophthalmic procedures while causing little to no irritation of the surrounding tissue.

It is further an object of the invention to provide the ophthalmic sutures having a higher tensile strength than commonly employed ophthalmic suture materials of a similar diameter.

It is further an object of the invention to provide methods of making ophthalmic sutures that are biocompatible and biodegradable and capable of delivering one or more therapeutic agents.

It is further an object of the invention to provide method of ophthalmic surgery and repair using the sutures described herein to increase patient comfort and/or success as compared to traditional ophthalmic suture materials.

SUMMARY OF THE INVENTION

Ophthalmic suture materials made from biocompatible and biodegradable polymers with high tensile strength for use in drug delivery, methods of making them, and method of using them for ocular surgery and repair have been developed. The suture materials are made from a combination of a biodegradable, biocompatible polymer and a hydrophilic biocompatible polymer. In a preferred embodiment the suture materials are made from a poly(hydroxyl acid) such as poly(l-lactic acid) and a polyalkylene oxide such as poly(ethylene glycol) or a polyalkylene oxide block copolymer. The sutures entrap (e.g., encapsulate) one or more therapeutic, prophylactic or diagnostic agents and provide prolonged release over a period of at least a week, preferably a month.

Exemplary agents include, but are not limited to, anti-inflammatory agents such as dexamethasone, prednisolone, triamcinolone, and flurbiprofen, released in an effective amount to prevent post-operative inflammation resulting from the ophthalmic procedure or from the presence of the suture. Other therapeutic agents include neomycin, polymyxin B, bacitracin, gramicidin, gentamicin, oyxtetracycline, ciprofloxacin, ofloxacin, miconazole, itraconazole, trifluridine, and vidarabine to prevent or inhibit the occurrence of post-operative ocular infections. Sutures release anti-infective agents for a period of at least seven days, more preferably 30 days, in an effective amount to prevent infection.

The sutures can be monofilament, multi-filament or braided sutures. For use in ophthalmic procedures, the sutures will typically have a diameter of between approximately 10 µm and 100 µm, preferably between 10 µm and 90 µm, more preferably between about 10 µm to about 70 µm, most preferably between about 20 µm and 60 µm. In particular embodiments, the diameter is between about 40 µm and 50 µm. The fiber diameters in the examples correspond to 7.0 to 10.0 (USP designation), diameters commonly used in ophthalmic surgeries. To prevent suture breakage while maintaining flexibility and patient comfort, the sutures maintain high tensile strengths even at smaller overall diameters. In a preferred embodiment, a biodegradable suture material is provided having a diameter of less than 80 µm and a tensile strength of greater than 700 MPa, preferably greater than 1.0 GPa.

DETAILED DESCRIPTION OF THE INVENTION

Figure 1:
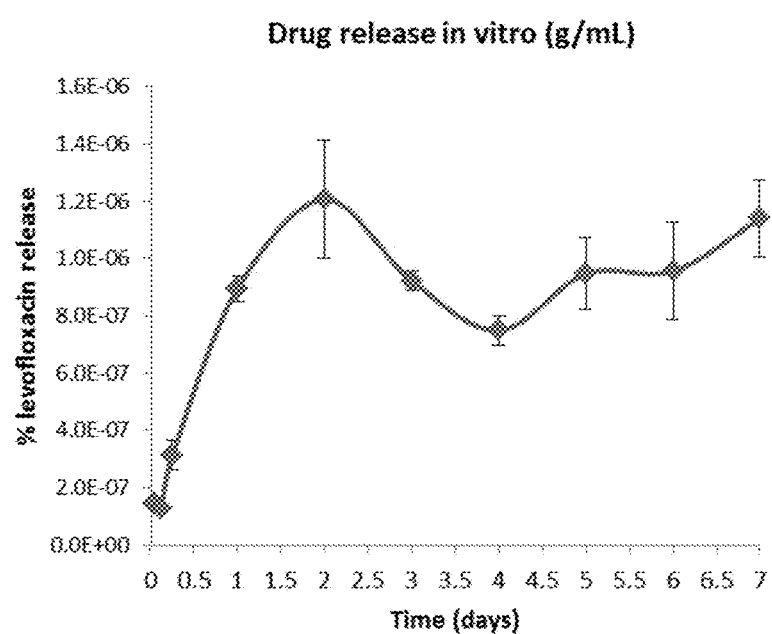
FIG. 1 is a graph showing the in vitro drug release in PBS buffer (% release) as a function of time (days) for 1 cm of levofloxacin-PLLA-PEG 2% fibers prepared in Example 1.

Biodegradable ophthalmic sutures and suture materials are provided made from a biodegradable, biocompatible polymer. An exemplary biodegradable, biocompatible polymer is poly(l-lactic acid) (PLLA). The sutures in some embodiments contain one or more hydrophilic polymers, preferably poly(ethylene glycol) (PEG). The sutures contain one or more therapeutic, prophylactic, or diagnostic agents. In preferred embodiments, the suture contains anti-infective agents and/or anti-inflammatory agents.

I. Definitions

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups.

In preferred embodiments, a straight chain or branched chain alkyl has 30 or fewer carbon atoms in its backbone (e.g., $C_1$-$C_{30}$ for straight chains, $C_3$-$C_{30}$ for branched chains), preferably 20 or fewer, more preferably 15 or fewer, most preferably 10 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a hosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

The terms "biocompatible" and "biologically compatible", as used interchangeably herein, refer to materials that are, with any metabolites or degradation products thereof, generally non-toxic to the recipient, and cause no significant adverse effects to the recipient. Generally speaking, biocompatible materials are materials which do not elicit a significant inflammatory or immune response when administered to a patient. In some embodiments a biocompatible material elicits no detectable change in one or more biomarkers indicative of an immune response. In some embodiments, a biocompatible material elicits no greater than a 10% change, no greater than a 20% change, or no greater than a 40% change in one or more biomarkers indicative of an immune response.

The term "biodegradable", as used herein, means that the material, fiber or suture degrades or breaks down into its component subunits, or digestion products, e.g., by a biochemical process, of the material into smaller (e.g., non-polymeric) subunits. In some embodiments, a biodegradable material, fiber or suture degrades into $CO_2$, $H_2O$, and other biomass materials. In some embodiments, the degradation occurs over a period less than 30 days, less than 60 days, less than 90 days, less than 120 days, less than 180 days, less than 1 year. In some embodiments the degradation occurs over a period greater than 30 days, greater than 60 days, greater than 90 days, greater than 120 days, greater than 180 days, or greater than 1 year. In certain embodiments degradation of a material, fiber or suture is said to be complete when at least 80% by mass has degraded, when at least 85% by mass has degraded, when at least 90% by mass has degraded, when at least 95% by mass has degraded, or when at least 99% by mass has degraded. The biodegradation rate depends upon several factors, both environmental and material. Non-limiting examples of environmental factors influencing biodegradation rates include temperature, pH, oxygen concentrations, and microbial and enzymatic activities. Non-limiting examples of material properties influencing biodegradation rates include degree of branching of the polymer chains, the presence and amount of hydrophilic groups, stereochemistry, molecular weight, the degree of crystallinity, the crosslinking, surface roughness, and the surface to volume ratio.

The term "inhibit," "inhibiting," or "inhibition" refers to a decrease in activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The term "subject" refers to any individual who is the target of administration. The subject can be a vertebrate, for example, a mammal. Thus, the subject can be a human. The term does not denote a particular age or sex. The term "patient" refers to a subject afflicted with a disease or disorder. The term "patient" includes human and veterinary subjects. The term "patient" or "subject" to be treated refers to either a human or non-human animal.

The term "prodrug", as used herein, refers to compounds which, under physiological conditions, are converted into the therapeutically active agents of the present invention. A common method for making a prodrug is to include selected moieties which are hydrolyzed under physiological conditions to reveal the desired molecule. In other embodiments, the prodrug is converted by an enzymatic activity of the host animal.

The term "prevent," "preventing," or "prevention" does not require absolute forestalling of the condition or disease but can also include a reduction in the onset or severity of the disease or condition or inhibition of one or more symptoms of the disease or disorder.

The term "pharmaceutically acceptable salt", as used herein, refer to derivatives of the compounds defined herein, wherein the parent compound is modified by making acid or base salts thereof. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wermuth, Eds., Wiley-VCH, Weinheim, 2002.

As generally used herein "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "treat" or "treatment" refers to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

II. Ophthalmic Sutures
  A. Suture Properties
    1. Suture Diameter

Suture diameters are defined by the United States Pharmacopeia (U.S.P.). Modern sutures range from #5 (heavy braided suture for orthopedics) to #11-0 (fine monofilament suture for ophthalmics). Suitable diameters for ophthalmic use are USP size 6.0-11.0, preferably 7.0-11.0, more preferably 8.0-11.0, most preferably 9.0-11.0.

TABLE 1

Diameter for various USP size sutures as well as the Knot-pull tensile strength in Newtons and grams.

| USP Size | Limits on Average φ (μm) | | Knot-pull tensile strength (N) | Knot-pull tensile strength (g) |
| --- | --- | --- | --- | --- |
| | Min | Max | | |
| 10-0 | 20 | 29 | 0.24* Straight pull | 24.47 |
| 9-0 | 30 | 39 | 0.49* | 49.96 |
| 8-0 | 40 | 49 | 0.69 | 70.36 |
| 7-0 | 50 | 69 | 1.37 | 139.70 |
| 6-0 | 70 | 99 | 2.45 | 249.83 |

Table 2 provides the Typical USP tensile strength values for various sized commercially available sutures.

TABLE 2

| Size | Diameter (mm) | Tensile Strength (Mpa) |
| --- | --- | --- |
| 9.00 | 0.030 | 693.56 |
| 8.00 | 0.040 | 549.36 |
| 7.00 | 0.050 | 698.09 |
| 6.00 | 0.070 | 636.94 |

The sutures can be multi-filament or braided sutures, or can be monofilament. For use in ophthalmic procedures, the sutures will typically have a diameter of approximately 10 μm (USP 11.0) to approximately 100 μm (USP 6.0), preferably 10 μm (USP 11.0) to about 70 μm (USP 7.0), more preferably from about 10 μm (USP 11.0) to about 50 μm (USP 8.0), most preferably from about 10 μm (USP 11.0) to about 40 μm (USP 9.0). In particular embodiments, the diameter is from about 20 μm to about 50 μm (USP 8.0, 9.0, or 10.0). USP 11.0 and 10.0 are often used in the most delicate surgeries, such as in the eye.

In other embodiments, the sutures have the above diameter and a tensile strength of at least about 600, 650, 700, 750, 800, 850, 900, 950, or 1000 MPa. In particular embodiments, the sutures have a tensile strength from about 1000 to about 2500 MPa, preferably from about 1200 to about 2500 MPa, more preferably from about 1300 to about 2300 MPa. The sutures should retain the tensile strength for the requisite period of time.

A. Biodegradable Polymers

The sutures contain one or more biodegradable, biocompatible polymers. The one or more biodegradable, biocompatible polymers can be homopolymers or copolymers.

Examples of suitable biodegradable, biocompatible polymers. include polyhydroxyacids such as poly(lactic acid), poly(glycolic acid), and poly(lactic acid-co-glycolic acids); polyhydroxyalkanoates such as poly-3-hydroxybutyrate or poly-4-hydroxybutyrate; polycaprolactones; poly(orthoesters); polyanhydrides; poly(phosphazenes); poly(hydroxyalkanoates); poly(lactide-co-caprolactones); polycarbonates such as tyrosine polycarbonates; polyamides (including synthetic and natural polyamides), polypeptides, and poly (amino acids); polyesteramides; polyesters; poly(dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly(maleic acids), as well as copolymers thereof.

In one embodiment, the biodegradable, biocompatible polymer is selected from the group consisting of polylactides, polyglycolides, poly(lactide-co-glycolide)s, polylactic acids, polyglycolic acids, poly(lactic acid-co-glycolic acid) s, polycaprolactones, polycarbonates, polyesteramides, polyanhydrides, poly(amino acids), polyorthoesters, polyacetyls, polycyanoacrylates, polyetheresters, polydioxanones, polyalkylene alkylates, copolymers of polyethylene glycol and polylactides or poly(lactide-co-glycolide)s, biodegradable polyurethanes, and certain types of protein and polysaccharide polymers, as well as blends and copolymers thereof. In a further embodiment, the biodegradable polymer is selected from the group consisting of polyhydroxy acids, polylactic acids, polylactides, polyglycolides, polyglycolic acids, and copolymers thereof as well as derivatives thereof. The biodegradable polymers may also include or consist of polyanhydrides, polyorthoesters, and polysaccharide polymers.

In one embodiment, the biodegradable polymer is poly-(D,L-lactide-co-glycolide). In some embodiments, the poly-(D,L-lactide-co-glycolide) contains about 55 to about 80 mole % lactide monomer and about 45 to about 20 mole % glycolide. The poly-(D,L-lactide-co-glycolide) may also contain about 65 to about 75 mole % lactide monomer and about 35 to about 25 mole % glycolide. The poly-(D,L-lactide-co-glycolide) can contain terminal acid groups.

The biodegradable, biocompatible polymer can be a polylactic acid polymer or copolymer containing lactide units substituted with alkyl moieties. Examples include, but are not limited to, poly(hexyl-substituted lactide) or poly(di-hexyl-substituted lactide).

The molecular weight of the one or more biodegradable, biocompatible polymer can be varied to prepare sutures and fibers having the desired properties, such as drug release rate, for specific applications. The one or more biodegradable, biocompatible polymers can have a molecular weight of about 150 Da to 1 MDa. In certain embodiments, the biodegradable, biocompatible polymers has a molecular weight of between about 1 kDa and about 200 kDa, more preferably between about 50 kDa and about 150 kDa.

The amount of polymer or polymers in the finished fibers can vary. In some embodiments, the concentration of the polymer or polymers in the finished fibers/sutures is from about 75 wt % to about 85% by weight of the finished fibers, preferably from about 77% to about 83% by weight of the finished fibers.

B. Hydrophilic Polymers

In some embodiments the suture contains one or more hydrophilic polymers. The hydrophilic polymer can be, for example, a poly(alkylene glycol), a polysaccharide, poly (vinyl alcohol), polypyrrolidone, a polyoxyethylene block copolymer (PLURONIC®) or a copolymers thereof. In preferred embodiments, the one or more hydrophilic polymers are, or are composed of, polyethylene glycol (PEG).

Each hydrophilic polymer can independently contain any hydrophilic, biocompatible (i.e., it does not induce a significant inflammatory or immune response), non-toxic polymer or copolymer. Examples of suitable polymers include, but are not limited to, poly(alkylene glycols) such as polyethylene glycol (PEG), poly(propylene glycol) (PPG), and copolymers of ethylene glycol and propylene glycol, poly (oxyethylated polyol), poly(olefinic alcohol), polyvinylpyrrolidone), poly(hydroxyalkylmethacrylamide), poly(hydroxyalkylmethacrylate), poly(saccharides), poly(amino acids), poly(hydroxy acids), poly(vinyl alcohol), and copolymers, terpolymers, and mixtures thereof.

In preferred embodiments, the one or more hydrophilic polymers are or contain a poly(alkylene glycol) chain. The poly(alkylene glycol) chains may contain between 1 and 500 repeat units, more preferably between 40 and 500 repeat units. Suitable poly(alkylene glycols) include polyethylene glycol, polypropylene 1,2-glycol, poly(propylene oxide), polypropylene 1,3-glycol, and copolymers thereof.

In some embodiments, the one or more hydrophilic polymers are copolymers containing one or more blocks of polyethylene oxide (PEO) along with one or more blocks composed of other biocompatible polymers (for example, poly(lactide), poly(glycolide), poly(lactide-co-glycolide), or polycaprolactone). The one or more hydrophilic polymer segments can be copolymers containing one or more blocks of PEO along with one or more blocks containing polypropylene oxide (PPO). Specific examples include triblock copolymers of PEO-PPO-PEO, such as POLOXAMERS™ and PLURONICS™.

In preferred embodiments, the one or more hydrophilic polymers are PEG chains. In such cases, the PEG chains can be linear or branched, such as those described in U.S. Pat. No. 5,932,462. In certain embodiments, the PEG chains are linear.

The amount of the hydrophilic polymer or polymers in the finished fibers can vary. In some embodiments, the amount of hydrophilic polymer or polymers in the finished fibers is from about 1% to about 10% by weight of the finished fibers, preferably from about 2% to about 5% by weight of the finished fibers, more preferably from about 3% to about 5% by weight of the finished fibers.

The inclusion of the hydrophilic polymer component in the ophthalmic sutures results in a significantly higher burst release and release of the agent over a longer period of time e.g., more than three months.

D. Active Agents

The sutures contain a therapeutic, diagnostic, and/or prophylactic agent. The active agent can be a small molecule active agent and/or a biomolecule, such as an enzyme, protein, growth factor, polypeptide, polysaccharide, lipid, or nucleic acid. Suitable small molecule active agents include organic and organometallic compounds. In some instances, the small molecule active agent has a molecular weight of less than about 2000 g/mol, preferably less than about 1500 g/mol, more preferably less than about 1200 g/mol, most preferably less than about 1000 g/mol. In other embodiments, the small molecule active agent has a molecular weight less than about 500 g/mol. The small molecule active agent can be a hydrophilic, hydrophobic, or amphiphilic compound. Biomolecules typically have a molecular weight of greater than about 2000 g/mol and may be composed of repeat units such as amino acids (peptide, proteins, enzymes, etc.) or nitrogenous base units (nucleic acids). In preferred embodiments, the active agent is an ophthalmic therapeutic, prophylactic or diagnostic agent. Non-limiting examples of ophthalmic agents include anti-glaucoma agents, anti-angiogenesis agents, anti-infective agents, anti-inflammatory agents, growth factors, immunosuppressant agents, anti-allergic agents, and combinations thereof.

Representative anti-glaucoma agents include prostaglandin analogs such as travoprost, bimatoprost, and latanoprost, beta-andrenergic receptor antagonists such as timolol, betaxolol, levobetaxolol, and carteolol, alpha-2 adrenergic receptor agonists such as brimonidine and apraclonidine), carbonic anhydrase inhibitors (such as brinzolamide, acetazolamine, and dorzolamide, miotics (i.e., parasympathomimetics, such as pilocarpine and ecothiopate), seretonergics muscarinics, dopaminergic agonists, and adrenergic agonists such as apraclonidine and brimonidine.

Representative anti-angiogenesis agents include, but are not limited to, antibodies to vascular endothelial growth factor (VEGF) such as bevacizumab (AVASTIN®) and rhuFAb V2 (ranibizumab, LUCENTIS®), and other anti-VEGF compounds; MACUGEN® (pegaptanim sodium, anti-VEGF aptamer or EYE001) (Eyetech Pharmaceuticals); pigment epithelium derived factor(s) (PEDF); COX-2 inhibitors such as celecoxib (CELEBREX®) and rofecoxib (VIOXX®); interferon alpha; interleukin-12 (IL-12); thalidomide (THALOMID®) and derivatives thereof such as lenalidomide (REVLIMID®); squalamine; endostatin; angiostatin; ribozyme inhibitors such as ANGIOZYME® (Sirna Therapeutics); multifunctional antiangiogenic agents such as NEOVASTAT® (AE-941) (Aeterna Laboratories, Quebec City, Canada); receptor tyrosine kinase (RTK) inhibitors such as sunitinib (SUTENT®); tyrosine kinase inhibitors such as sorafenib (Nexavar®) and erlotinib (Tarceva®); antibodies to the epidermal grown factor receptor such as panitumumab (VECTIBIX®) and cetuximab (ERBITUX®), as well as other anti-angiogenesis agents known in the art.

Anti-infective agents include antiviral agents, antibacterial agents, antiparasitic agents, and anti-fungal agents. Representative antiviral agents include ganciclovir and acyclovir. Representative antibiotic agents include aminoglycosides such as streptomycin, amikacin, gentamicin, and tobramycin, ansamycins such as geldanamycin and herbimycin, carbacephems, carbapenems, cephalosporins, glycopeptides such as vancomycin, teicoplanin, and telavancin, lincosamides, lipopeptides such as daptomycin, macrolides such as azithromycin, clarithromycin, dirithromycin, and erythromycin, monobactams, nitrofurans, penicillins, polypeptides such as bacitracin, colistin and polymyxin B, quinolones, sulfonamides, and tetracyclines. In a preferred embodiment the anti-infective agent is a fluoroquinolone, such as levofloxacin.

In some cases, the active agent is an anti-allergic agent such as olopatadine and epinastine.

Anti-inflammatory agents include both non-steroidal and steroidal anti-inflammatory agents. Suitable steroidal active agents include glucocorticoids, progestins, mineralocorticoids, and corticosteroids.

In particular embodiments, the therapeutic and/or prophylactic agent is selected from antibiotics, corticosteroids, anti-inflammatory agents, chemotherapeutic agents, immunosuppressant agents, and combinations thereof. Specific combinations include, but are not limited to, antibiotics and corticosteroids, antibiotics and anti-inflammatory agents, antibiotics and chemotherapeutic agents, and antibiotics and immunosuppressant agents.

The ophthalmic drug may be present in its neutral form, or in the form of a pharmaceutically acceptable salt. In some cases, it may be desirable to prepare a formulation containing a salt of an active agent due to one or more of the salt's advantageous physical properties, such as enhanced stability or a desirable solubility or dissolution profile.

Generally, pharmaceutically acceptable salts can be prepared by reaction of the free acid or base forms of an active agent with a stoichiometric amount of the appropriate base or acid in water or in an organic solvent, or in a mixture of the two; generally, non-aqueous media like ether, ethyl acetate, ethanol, isopropanol, or acetonitrile are preferred. Pharmaceutically acceptable salts include salts of an active agent derived from inorganic acids, organic acids, alkali metal salts, and alkaline earth metal salts as well as salts formed by reaction of the drug with a suitable organic ligand (e.g., quaternary ammonium salts). Lists of suitable salts are found, for example, in Remington's Pharmaceutical Sciences, 20th ed., Lippincott Williams & Wilkins, Baltimore, Md., 2000, p. 704. Examples of ophthalmic drugs sometimes administered in the form of a pharmaceutically acceptable salt include timolol maleate, brimonidine tartrate, and sodium diclofenac.

In some cases, the active agent is a diagnostic agent imaging or otherwise assessing the eye. Exemplary diagnostic agents include paramagnetic molecules, fluorescent compounds, magnetic molecules, and radionuclides, x-ray imaging agents, and contrast media.

The agent or agents can be directly dispersed or incorporated into the fibers as particles using common solvent with the polymer, for examples microparticles and/or nanoparticles of drug alone, or microparticles and/or nanoparticles containing a matrix, such as a polymer matrix, in which the agent or agents are encapsulated or otherwise associated with the particles.

The concentration of the drug in the finished fiber can vary. In some embodiments, the amount of drug is between about 0.1% and about 50% by weight, preferably between about 1% and about 40% by weight, more preferably between about 3% and about 40% by weight, most preferably between about 5% and about 40% by weight of the finished fibers.

In particular embodiments, the agent is an antimicrobial agent and the concentration of the agent is between about 30% to about 40% by weight of the finished fibers. The fiber releases an effective amount of the antimicrobial agent to inhibit/prevent bacterial growth for at least 2 weeks, 4 weeks, 6 weeks, 8 weeks, 10 weeks, 12 weeks, 16 weeks, or 20 weeks.

III. Methods of Making Sutures

The sutures can be prepared using techniques known in the art. In some embodiments, a polymer-drug solution is prepared by dissolving the polymers used to form the fiber matrix (e.g., biodegradable and/or biocompatible polymer), the agent to be delivered, and optionally a hydrophilic polymer or polymers. These materials are typically dissolved in an organic solvent, such as chloroform. The solutions can be maintained at room temperature and stirred until a homogeneous solution is obtained. In some embodiments, the solution is stirred at least one day, such as two days or three days.

The fibers can be prepared using a polymer extrusion system. In one embodiment, fiber extrusion platform includes a high voltage power supply, syringe pump, needle syringe and a grounded 20 cm diameter motor-run rotating metal disc. High voltage DC power was applied to the solution by clamping electrode on the blunted needle. With 5 kV applied voltage and the 12 ml/h feed rate, applied voltage initiates a polymer jet, which lands in 100% ethanol (Pharmco-Aaper, Brookfield, Conn.) bath on the metal disk to extract the solvent. The liquid reservoir was 5 cm away from the needle opening. Angular velocity of the collection wheel was adjusted by a DC motor controller (Dart 15DVE) unit, usually in the range of 20–40 rotation/min or 20-40 cm/sec. The fibers were collected from the disc and dried in a vacuum chamber for two days, allowing the solvents to evaporate. The fibers were then stored in dry conditions and kept in −20° C. for further analyses. The same procedure was repeated with the control solution.

III. Methods of Using

The fibers can be used simultaneously as drug delivery vehicles and sutures to close wounds in the eye, such as those created in ophthalmologic surgery or due to injury or trauma to the eye. The sutures can be modified by inclusion of a hydrophilic polymer such as PEG or a POLOXAMER® to provide a burst release of an active agent, such as an antimicrobial agent, followed by sustained release over an extended period of time, such as one week, two weeks, 4 weeks, 6 weeks, 8 weeks, 10 weeks, 12 weeks, 14 weeks, 16 weeks, 18 weeks, or 20 weeks.

The sutures typically have a diameter from about 20 to about microns, preferably from 30 to about 50 microns, more preferably from about 40 to about 50 microns. The sutures typically have a tensile strength of at least about 700, 800, 900, 1000, 1100, 1200, 1300, 1400, 1500, 1600, 1700, or 1800 MPa.

The sutures can be used in a variety of ophthalmic procedures known in the art. Examples include, but are not limited to, trabeculectomy as well as pterygium removal, cataract surgery, strabismus correction surgery, penetrating keratoplasty, sclerectomy, and conjunctival closure.

Trabeculectomy is an ophthalmic surgical procedure used in the treatment of glaucoma. Removing part of the eye's trabecular meshwork and adjacent structures allows drainage of aqueous humor from within the eye to underneath the conjunctiva to relieve intraocular pressure. The scleral flap is typically sutured loosely back in place with several sutures. Common complications include blebitis (an isolated bleb infection typically caused by microorganisms such as *Staphylococcus epidermidis, Propriobacterium acnes,* or *Staphylococcus aureus*), inflammation, and bleb-associated endophthalmitis.

Endophthalmitis is an inflammation of the ocular cavities and their adjacent structures. It is a possible complication of all intraocular surgeries, particularly cataract surgery, which can result in loss of vision or the eye itself. Endophthalmitis is usually accompanied by severe pain, loss of vision, and redness of the conjunctiva and the underlying episclera. Infectious etiology is the most common and various bacteria and fungi have been isolated as the cause of the endophthalmitis. The patient needs urgent examination by an ophthalmologist and/or vitreo-retina specialist who will usually decide for urgent intervention to provide intravitreal injection of potent antibiotics and also prepare for an urgent pars plana vitrectomy as needed. Enucleation may be required to remove a blind and painful eye.

Ideally, ophthalmic suture materials would be biodegradable and biodegradable over the useful suture lifetime, retaining the requisite tensile strength and capable of delivering therapeutic or prophylactic agents to increase patient success, however, it is not essential the suture be biodegradable. For pterygium removal, cataract surgery and strabismus correction surgery, sutures can be used to close the wound and release antibiotic and anti-inflammatory drugs. For trabeculectomy surgeries, sutures can be placed on sclera flaps providing local chemotherapeutic agents, decreasing production of scar tissue, and on conjunctival closure with antibiotic release. In penetrating keratoplasty, the sutures hold the graft, as well as release antibiotic and immunosuppressant agents.

EXAMPLES

Example 1

Levofloxacin-containing (L-lactic acid) (PLLA) Microfibers

Polymer and drug were dissolved in chloroform and the resulting solution was electrospun to form the fibers. The suture average diameter was 46±8 µm and the stress 61±1 MPa.

For the in vitro drug release assay, four milligrams of fibers were weighed, placed in tubes filled with buffered saline, and kept in an incubator shaker at 37° C. for 10 days. The in vitro release assay was carried out in triplicate. At selected intervals, supernatant was tested with high performance liquid chromatography (HPLC) to quantify the drug release. The fibers were morphologically evaluated by light and scanning electron microscopy and the tensile strength measured. HPLC demonstrated drug release within the first hour followed by a sustained release for at least ten days.

Antibacterial efficacy was performed against *Staphylococcus epidermidis*, by placing a piece of fiber on agar plate and incubating overnight at 37° C. Levofloxacin, a third-generation fluoroquinolone, was released from microfibers and showed activity against *S. epidermidis*, one of the most common bacteria residing on the ocular surface.

The PLLA used in these experiments is a biodegradable synthetic polymer and has been shown to have no cellular toxicity. This study showed that drug-loaded microfibers have great potential as sutures capable of local drug delivery in ophthalmic surgery.

Example 2

Preparation of Drug-loaded Polymeric Sutures Containing Hydrophilic Polymer

Polymer Solution

Levofloxacin loaded PLLA-PEG sutures were prepared having different concentrations of PEG. An initial polymer-drug solution was prepared by dissolving PEG (Sigma-Aldrich, St. Louis, Mo.) at either 1 wt %, 2 wt %, or 4 wt %, along with 20 wt % of levofloxacin and 76 wt % of PLLA(Mw=220,000 g/mol, PURAC Biochem, The Netherlands) in chloroform (Sigma-Aldrich, St Louis, Mo.). A control solution was prepared in the same manner, however no levofloxacin was included. A PLLA-F 127 suture was prepared from an initial polymer-drug solution prepared by dissolving Pluronic-F 127 (2 wt %) with 20 wt % of levofloxacin and 78 wt % of PLLA in chloroform. All solutions were kept at room temperature and stirred for approximately three days, resulting in homogeneous, viscous solutions.

Polymer Extrusion System

The experimental set up was a polymer extrusion system having a high voltage power supply, a syringe pump, a needle syringe and a grounded 20 cm diameter motor-run rotating metal disc. High voltage DC power was applied to the solution by clamping an electrode on the blunted needle. With 5 kV applied voltage and a 12 ml/h feed rate, applied voltage initiates a polymer jet, which contacts a 100% ethanol (Pharmco-Aaper, Brookfield, Conn.) bath on the metal disk to extract the solvent. The liquid reservoir was 5 cm away from the needle opening. Angular velocity of the collection wheel was adjusted by a DC motor controller (Dart 15DVE) unit, usually in the range of 20-40 rotation/min (corresponding to a distance of approximately 20-40 cm/sec). The fibers were collected from the disc and dried in a vacuum chamber for two days, allowing the solvents to evaporate. The fibers were then stored in dry conditions and kept at –20° C. for further analyses. The same procedure was repeated with the control solution.

Upon drying, the levofloxacin loaded PLLA-PEG fibers prepared from the 1 wt % PEG solution (PLLA-PEG 1%) contained approximately 1 wt % PEG and 10 wt % levofloxacin. Upon drying, the levofloxacin loaded PLLA-PEG fibers prepared from the 2 wt % PEG solution (PLLA-PEG 2%) contained approximately 2 wt % PEG and approximately 10 wt % levofloxacin. Upon drying, the levofloxacin loaded PLLA-PEG fibers prepared from the 4 wt % PEG solution (PLLA-PEG 4%) contained approximately 4 wt % PEG and approximately 10 wt % levofloxacin. Assuming all chloroform is remoed upon drying, the percentages of PEG in the dried suture is 1%, 2, and 4%, and the percentage of levofloxacin is 10%.

Example 3

Characterization of Drug-loaded, Polymeric Sutures

HPLC Analysis

Samples were analyzed using a Waters 1525 binary HPLC separation module, equipped with a Waters In-Line degasser AF, a Waters 717 plus autosampler (kept at 4° C.), a Waters 2998 photodiode array detector, a Water 2475 multi λ fluorescence detector, controlled by Waters Empower software. Isocratic separations were run on a Waters Symmetry™ 300 C18 5 µm column with 0.1% v/v TFA in $H_2O$: ACN (85:15 v/v) at flow rate 1 mL/min. Elution was simultaneously monitored by PDA detector (collecting UV-Vis spectra from 190-800 nm every 2 seconds, which can be used to obtain chromatograms at the desired wavelength in this range and UV-Vis profile of eluting compound present within given peak) as well as fluorescence detector with 1 channel set to detect the Levofloxacin with excitation at 290 nm and emission at 502 nm.

To obtain calibration curves and determine the limits of detection (LOD) for Levofloxacin, different amounts of drug (ranging from 1 pico gram to 1 micro gram) were injected on the column and used as external standard for quantification of the drug release from the fiber in vitro Excellent linearity (R=0.997) in the wide concentration range for the drug was observed. Measured limits of detection for Levofloxacin using absorbance at 295 nm and florescence (ex295/502 nm) were 1 ng with N/S=6.46 (noise to signal ratio) and 1 pg with N/S=13.67 injected on the column, respectively. Triplicated injections of 100 µL for each sample were performed. The use of a PDA detector allowed for a confident assignment of the peak related to Levofloxacin, not only based on its retention time but also based on its UV-Vis profile.

Fluorescence Spectroscopy

To obtain the optimal conditions for the Levofloxacin, fluorescence spectra of were recorded in 0.1% TFA in a solution containing water:acetonitrile (85:15 v/v) and at concentration of $1\times10^{-6}$ g/mL, using a Shimadzu RF-5301 Spectrofluorometer.

Drug Release In Vitro

One centimeter of fiber from Example 1 was placed in 1 mL of PBS buffer (Dulbecco's Phosphate Buffered Saline 1×, ATCC, Manassas, Va.) and incubated for 1 hour, 3 hours, 6 hours, 1 day, 2 days, 3 days, 4 days, 5 days, 6 days, and 7 days. For each time point 6 samples were prepared. After incubation at each time point fibers were retrieved for agar plate studies and obtained solutions were analyzed by HPLC to determine the amount of drug released. As shown in FIG. 1, release of levofloxacin was relatively uniform over the seven-day test period. The % release of levofloxacin reached a maximum by day 2 and remained between $5 \times 10^{-7}$% and $15 \times 10^{-7}$ through day 7.

Figure 2:
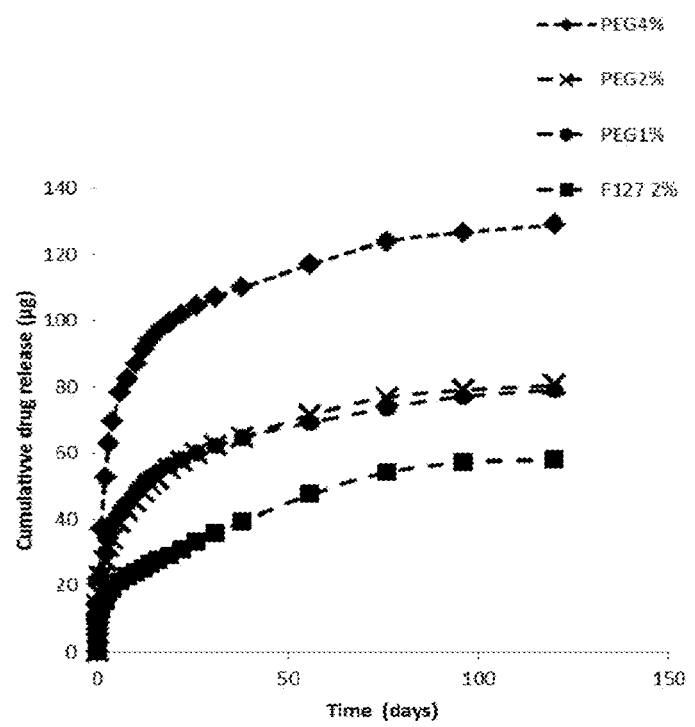
FIG. 2 is a graph showing the in vitro drug release of 4 mg of levofloxacin loaded PLLA-PEG and PLLA-F127 fibers in tubes filled with PBS and kept in an incubator shaker.

FIG. 2 shows the cumulative drug release for fibers prepared from 1% PEG, 2% PEG, 4% PEG, and 2% F 127. Fibers prepared from 4% PEG exhibit the largest burst release and the highest cumulative drug release over time. Fibers prepared from 1% PEG and 2% PEG exhibit almost identical release curves. Fibers prepared from 2% Pluronic exhibited little burst release and release the least amount of drug over the time. This may be due to the presence of the more hydrophobic propylene oxide segments in the F 127.

Morphology

The fibers were morphologically evaluated by light microscope (Zeiss) and scanning electron microscope (LEO Field Emission SEM, LEO/Zeiss Field-emission SEM, Germany). Under SEM, the fibers appeared to have a smooth surface with porosity. The average diameters are listed in Table 3. According to data from United States Pharmacopeia (USP) the fiber diameters correspond to 7-0 to 10-0 fibers (USP designation), diameters that are commonly used in ophthalmic surgeries. There are no sutures commercially available for ophthalmic surgeries that can locally release drugs to prevent or inhibit infection, rejection, or inflammation.

TABLE 3

Average diameters (μm) of levofloxacin loaded PLLA-PEG and PLLA-F127 fibers.

| PEG 4% | | PEG 2% | | PEG 1% | | F127 % | |
| --- | --- | --- | --- | --- | --- | --- | --- |
| AV | SD | AV | SD | AV | SD | AV | SD |
| 61.4 | ±8.4 | 37.5 | ±7.4 | 82.6 | ±22.2 | 76.6 | ±5.1 |

Mechanical Testing

Tensile tests over single polymer string were performed with a DMA Q800 unit (TA Instruments, New Castle, Del.). Samples of 5 mm of length were all in string form and their diameters were determined with light microscopy. Other parameters like length and force were measured and controlled by equipment. All samples were stretched until breaking. Sample modulus was calculated with the linear segment of the stretch and strain curves. Both microfibers levofloxacin-PLLA-PEG and PLLA-PEG had an average tensile strength of 1.8 GPa±457 MPa.

Example 4

In Vivo Studies of Drug-loaded, Polymeric Sutures

Fifteen female Sprague-Dawley rats (Taconic Farms, Inc., Germantown, N.Y.), weighing approximately 200-300 g, were intraperitoneally anesthetized with a Ketamine (75 mg/Kg)/Xylazine (5 mg/Kg) (Sigma-Aldrich, St. Louis, Mo.) combination. A drop of proparacaine hydrochloride ophthalmic solution 0.5% (Bausch & Lomb Inc., Tampa, Fla.) was applied to the cornea. Throughout the animal study, the protocol of the "ARVO Statement for the Use of Animals in Ophthalmic and Vision Research" was followed.

The 15 rats were divided into three groups consisting of a control 9-0 Nylon suture, a control PLLA-PEG 2% suture, and a drug loaded levofloxacin-PLLA-PEG 2% suture. Approximately 1 cm of suture was placed into the corneal stroma.

Figure 3:
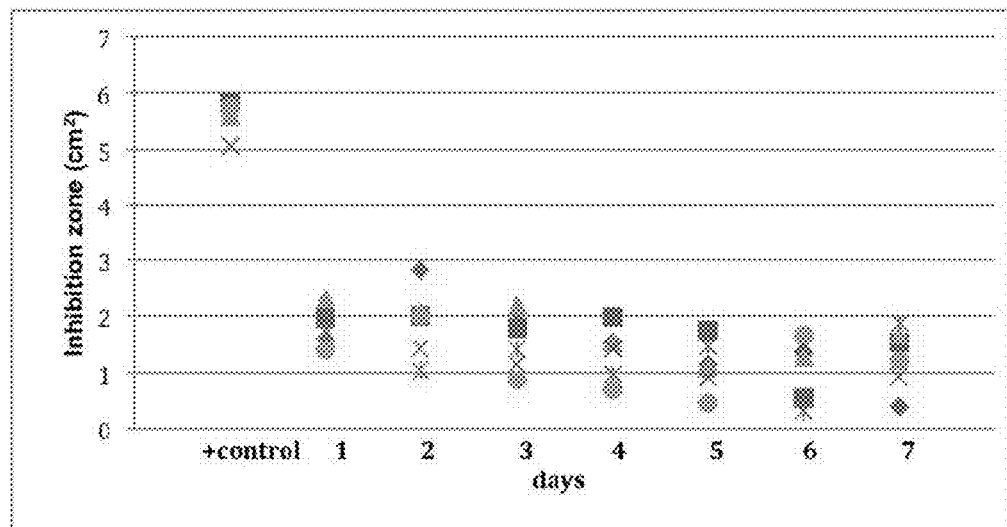
FIG. 3 is a graph showing the amount of levofloxacin released (ng) into the aqueous humor, the cornea, and in total from approximately 1 cm ophthalmic sutures made from PLLA-PEG fibers placed on the corneal stroma of female Sprague-Dawley rats as a function of time (hours)

The rats were evaluated for signs of infection every two days after the surgery. Seven days after the placement of the sutures the rats were euthanized and the corneas extracted and fixed for 24 hours in 4% paraformaldehyde. The corneas were embedded in paraffin, cross sectioned, and stained with hematoxylin and eosin for further microscopic study. The distribution of the active agent in the eye is described in Table 4. The data in Table 4 is shown graphically in FIG. 3.

TABLE 4

Amount of drug detected in the cornea, in the aqueous humor, remaining in the suture and the total amount of drug detected and released from an approximately 1 cm suture prepared from levofloxacin loaded PLLA-PEG 2% fibers and placed on the corneal stroma of female Sprague-Dawley rats as a function of time (hours).

| Time (hrs) | Cornea (ng) | Aqueous (ng) | Remained in suture (ng) | Total drug detected (ng) | drug released (ng) |
| --- | --- | --- | --- | --- | --- |
| 2 | 2.90 | 0.85 | 1531.76 | 1535.51 | 436.01 |
| 4 | 2.00 | 0.86 | 895.62 | 898.49 | 1069.28 |
| 6 | 7.23 | 0.42 | 665.93 | 673.58 | 1294.19 |
| 8 | 1.51 | 0.18 | 635.34 | 637.03 | 1330.74 |
| 12 | 1.48 | 0.35 | 894.58 | 896.41 | 1071.36 |
| 24 | 0.28 | 0.00 | 474.87 | 475.15 | 1492.62 |
| 48 | 2.73 | 0.00 | 818.47 | 821.21 | 1146.56 |
| 72 | 1.22 | 0.04 | 1088.25 | 1089.51 | 878.26 |
| 96 | 1.15 | 0.02 | 695.97 | 697.14 | 1270.63 |
| 120 | 0.46 | 0.18 | 1291.13 | 1291.78 | 675.99 |
| 144 | 1.35 | 0.18 | 477.30 | 478.84 | 1488.93 |
| 168 | 0.51 | 0.04 | 522.85 | 523.40 | 1444.37 |

Example 5

In Vitro Antibacterial Study of Drug-loaded, Polymeric Sutures

Bacteria Inhibition Zone

Fiber samples were incubated in PBS buffer to measure the drug release for 1 to 7 days at 37° C. The fibers were retrieved and incubated at 37° C. overnight on LB agar plates (Sigma-Aldrich, St Louis, Mo.) inoculated with *Staphylococcus epidermidis* (ATCC, Manassas, Va.) to evaluate the inhibition of bacteria growth. Zones of microbial inhibition around the drug-loaded fibers were measured at 24 hours. Negative and positive controls were done as well. The bacteria inhibition zone showed that antibiotic was released from the microfiber in a necessary amount to inhibit/prevent bacteria growth around it.

Figure 4:
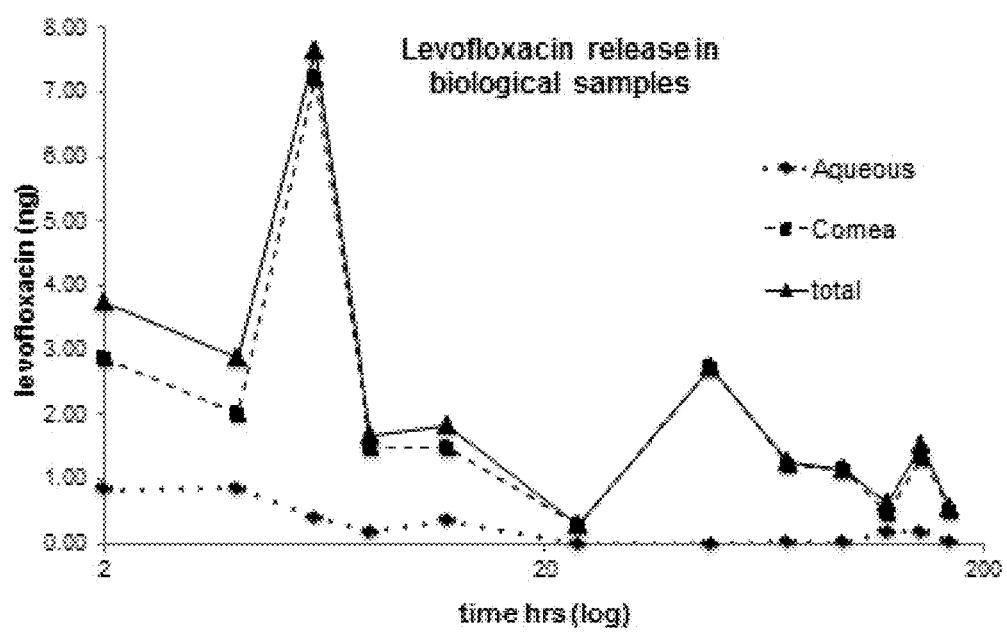
FIG. 4 is a graph showing the inhibition zone of bacterial growth ($cm^2$) as a function of the time (days) for levofloxacin-PLLA-PEG fibers incubated in PBS buffer and measured via retrieval and incubation at 37° C. overnight (24 hours) on LB agar plates inoculated with *Staphylococcus epidermidis* Negative and positive controls were done as well.

The quantification of the bacterial inhibition zone is shown in FIG. 4. Drug release in vitro, measured by high performance liquid chromatography (HPLC) showed a sustained and detected drug release for more than 3 months at a level capable of inhibiting/preventing bacterial growth.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of making a suture between about 10 microns and about 100 microns in diameter and having a tensile strength between about 700 MPa and about 2.5 GPa comprising one or more fibers, comprising
    extruding a jet onto a spinning device, wherein the jet comprises an electrically charged solution comprising a biodegradable, biocompatible hydrophobic polymer and a hydrophilic polymer, and optionally one or more therapeutic, diagnostic, or prophylactic agents in a solvent,
    and drying the jet to form fibers,
    wherein the amount of the hydrophilic polymer is between about 1 and about 10% by weight of the finished fiber.

2. The method of claim 1, wherein the spinning device contains another solvent capable of extracting the solvent of the jet upon contact.

3. The method of claim 1, wherein the spinning device has an angular velocity in the range between 20 to 40 rotations per minute or permits a travel distance between 20 and 40 centimeters per second.

4. The method of claim 1, wherein the jet is dried by evaporating the solvent in a vacuum chamber.

5. The method of claim 1, wherein the suture is in the form of a braided or multifiber suture.

6. The method of claim 1, wherein the suture has a diameter between about 20 μm and 90 μm.

7. The method of claim 1, wherein the suture has a diameter between 20 μm and 60 μm.

8. The method of claim 1, wherein the suture has a tensile strength between 1.3 GPa and 2.3 GPa.

9. The method of claim 1, wherein the biodegradable, biocompatible hydrophobic polymer comprises a biodegradable, biocompatible polymer selected from the group consisting of polyhydroxyacids, polyhydroxyalkanoates, polycaprolactones, polyanhydrides, polyesters, hydrophobic polyethers, and copolymers thereof.

10. The method of claim 1, wherein the hydrophilic polymer is selected from the group consisting of a poly (alkylene glycol), a polysaccharide, poly(vinyl alcohol), polypyrrolidone, a polyoxyethylene block copolymer, or a copolymers thereof.

11. The method of claim 10, wherein the amount of the hydrophilic polymer is between about 2% and about 5% by weight of the finished fibers.

12. The method of claim 1, wherein the solution comprises one or more therapeutic agents selected from the group consisting of anti-glaucoma agents, anti-angiogenesis agents, anti-infective agents, anti-inflammatory agents, growth factors, immunosuppressant agents, anti-allergic agents, and combinations thereof.

13. The method of claim 12, wherein the anti-infective agent is levofloxacin.

14. The method of claim 1, wherein the solution comprises one or more therapeutic, diagnostic, or prophylactic agents providing sustained release over at least seven days after placement.

15. The method of claim 9, wherein the amount of the biodegradable, biocompatible polymer is between about 75% and about 85% by weight of the finished fibers.

16. The method of claim 1, wherein the amount of the therapeutic, prophylactic, or diagnostic agent is between about 0.1% and about 50% by weight of the finished fibers.

* * * * *